United States Patent [19]
Cohn

[11] Patent Number: 4,940,458
[45] Date of Patent: Jul. 10, 1990

[54] EPIDURAL NEEDLE PLACEMENT SYSTEM

[76] Inventor: Arnold K. Cohn, 1415 Meadow La., Glenview, Ill. 60025

[21] Appl. No.: 305,784

[22] Filed: Feb. 2, 1989

[51] Int. Cl.$^5$ .............................................. A61M 5/00
[52] U.S. Cl. ..................................... 604/51; 604/117; 604/158; 128/745
[58] Field of Search .............. 604/275, 272, 164, 165, 604/156, 117, 118, 170, 158, 159, 51; 128/748

[56] References Cited
U.S. PATENT DOCUMENTS

| 1,087,845 | 2/1914 | Stevens | 604/159 |
| 2,001,638 | 5/1935 | Tornsjo | 604/117 |
| 4,763,667 | 8/1988 | Manzo | 604/164 |
| 4,796,641 | 6/1989 | Mills et al. | 128/673 |
| 4,828,547 | 5/1989 | Sahi et al. | 604/164 |

Primary Examiner—Stephen C. Pellegrino
Attorney, Agent, or Firm—Dressler, Goldsmith, Shore, Sutker & Milnamow, Ltd.

[57] ABSTRACT

An epidural needle placement system and procedure comprising a hollow barrel and an epidural needle for insertion therein that is adapted to be advanced in a controlled manner.

2 Claims, 2 Drawing Sheets

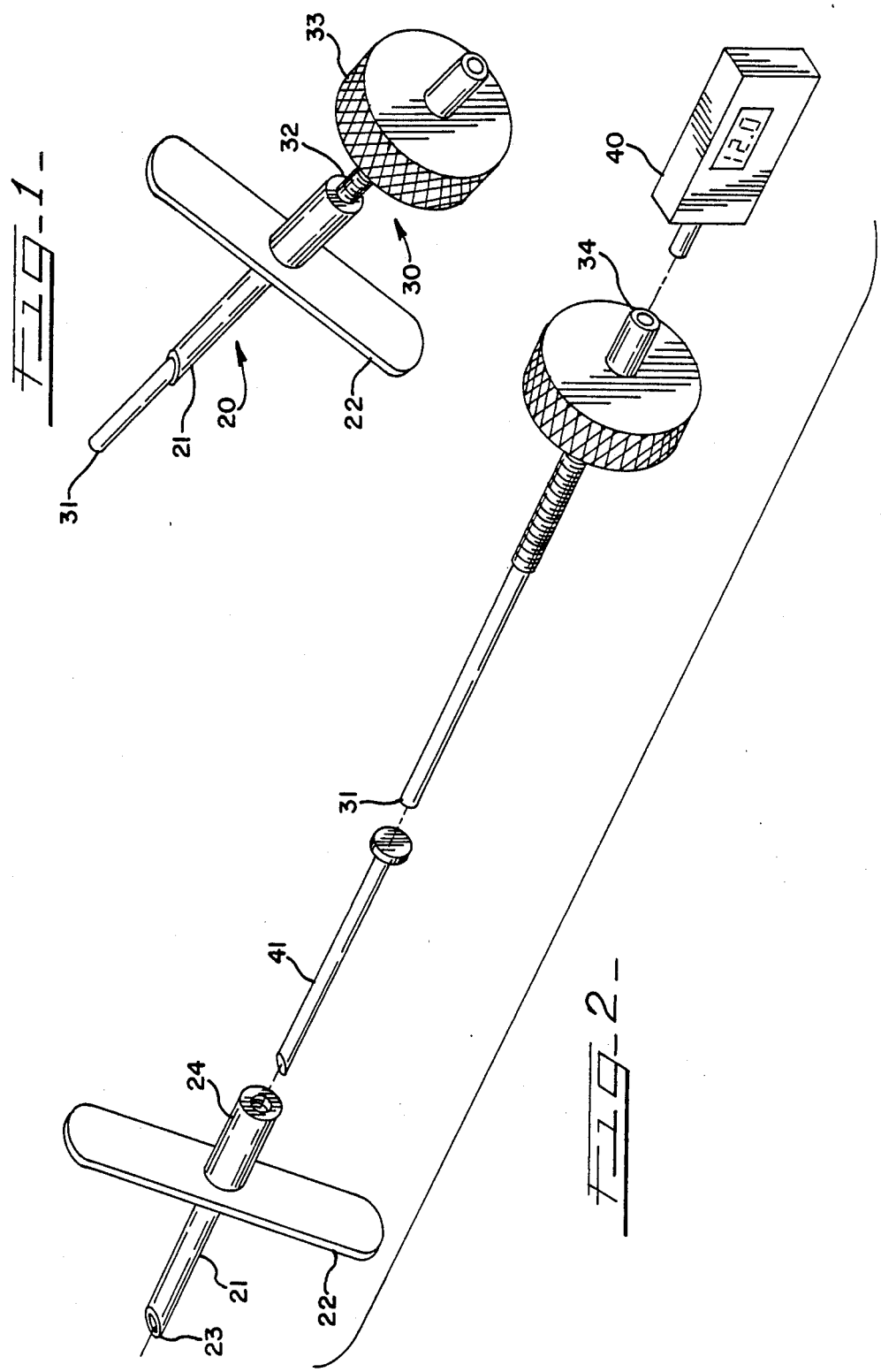

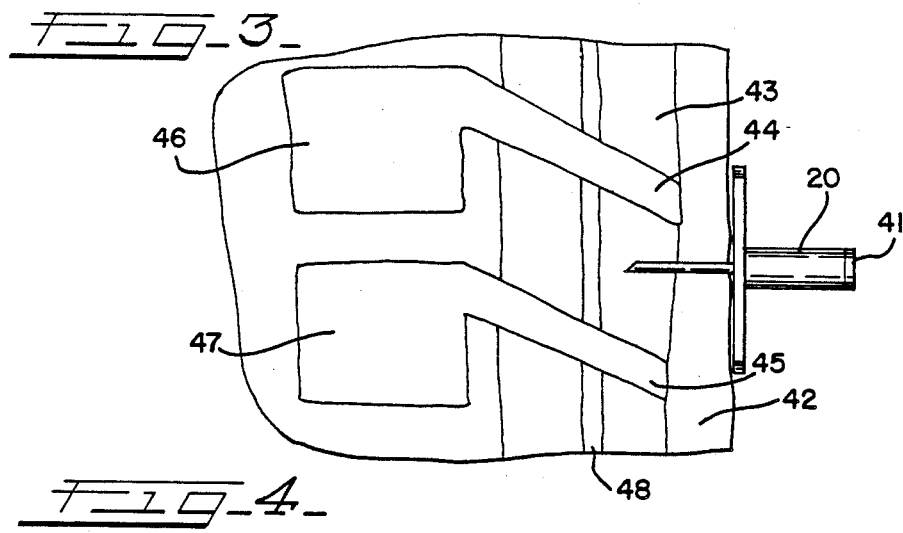
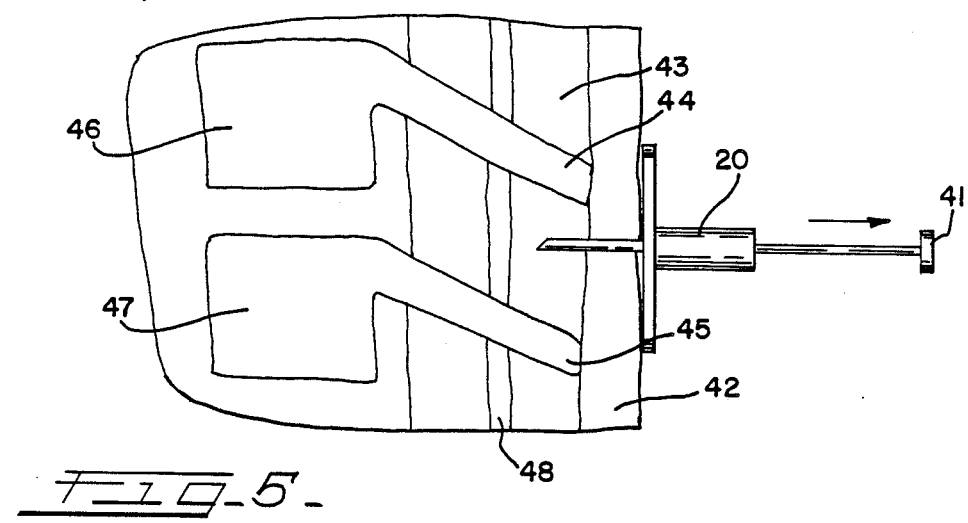
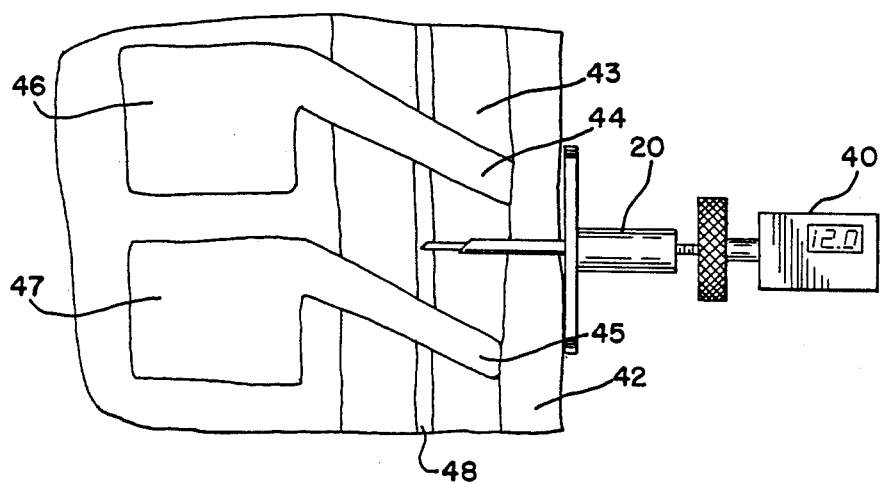

EPIDURAL NEEDLE PLACEMENT SYSTEM

BACKGROUND OF THE INVENTION

Epidural needle and catheter placement procedures are widely utilized for a variety of medical purposes. For example, anesthetics are often administered through a needle placed in the epidural space, or through a catheter which has been inserted into the epidural space after the space has been located with a needle. Analgesics, corticosteroids and other therapeutic agents are also administered via this route for the treatment of a variety of conditions such as radicular back pain and post-surgical epidural fibrosis.

The epidural space or cavity is the space between the spinal dura or fibrous membrane forming the outermost covering of the spinal cord and the periosteum or membrane lining the spinal canal. When administering anesthetics or therapeutic agents, it is important to precisely locate the epidural space. If the needle is not deep enough, the anesthetic or therapeutic agent will not reach the targeted site and if the needle penetrates too far, spinal puncture or other complications may result.

Current techniques for inserting needles into the epidural space have many disadvantages. The needle is advanced manually in very small increments and air or saline is repeatedly injected into the needle until a pressure drop is observed due to a sudden decrease in the resistance to injection when the needle enters the epidural space. This procedure is tedious, difficult to control and can result in puncture of, or injury to the dura.

It is therefore an object of this invention to provide a device and procedure for epidural needle placement which overcomes the aforementioned disadvantages and is accurate and easy to utilize.

SUMMARY OF THE INVENTION

The present invention is directed to an epidural needle placement device and procedure which utilizes device having a threaded barrel and a correspondingly threaded blunt-tipped epidural needle. The device may also include a small solid state pressure monitor and a stylet for initial insertion into the barrel when the barrel is first placed into the interspinous ligament.

The device of the present invention will allow for rapid insertion of a needle into the epidural space in a controlled manner with prompt confirmation of penetration into the epidural space as contrasted to the tedious and inaccurate techniques currently in use.

BRIEF DESCRIPTION OF THE DRAWINGS

The present invention will best be understood by reference to the following specification taken in conjunction with the accompanying drawings in which:

FIG. 1 is a simplified perspective view of an embodiment of the present invention;

FIG. 2 is an exploded perspective view of an embodiment of the present invention;

FIG. 3 is a view of an embodiment of the present invention in a first operational position with respect to the epidural space;

FIG. 4 is a view of the embodiment of FIG. 3 in a second operational position with respect to the epidural space; and FIG. 5 is a view of the embodiment of FIG. 3 in a third operational position with respect to the epidural space.

DETAILED DESCRIPTION OF THE PREFERRED EMBODIMENT

While the present invention is susceptible of embodiment in many forms, there is shown in the drawings and will hereinafter be described a presently preferred embodiment with the understanding that the present specification is to be considered as an exemplification of the invention, and is not intended to limit the invention to the specific embodiment illustrated.

Referring to the drawings, FIG. 1 is a simplified perspective view of an embodiment of the device 10 of the present invention. The device 10 includes an internally threaded barrel 20, a correspondingly externally threaded, blunt-tipped hollow epidural needle 30 and a small, preferably solid state pressure monitor 40.

The threaded barrel 20 includes a hollow portion 21, approximately 16 to 18 guage in size. It also has a large flat tab or ridge 22 to anchor it against the patient's skin and prevent too much penetration or ingestion of the barrel 20 so that the sharp tip 23 of the barrel 20 does not enter the epidural space of the patient. The tab 22 also prevents the device 10 from being pulled out of the patient. The upper portion 24 of the barrel 20 has internal threads.

The hollow epidural needle 30 has a blunt tip 31 to help avoid dural puncture. The upper portion 32 of the epidural needle 30 has external threads that correspond to the internal threads on the barrel 20. A knurled wheel or knob 33 is located at the proximal end of the needle 30 to enable precise control of the penetration of the tip 31 of the needle 30 which is advanced by rotating the knurled wheel 33 in a clockwise direction while the external threads of the epidural needle 30 engage the internal threads of the barrel 20. The tip 31 of the needle 30 should not extend beyond the tip 23 of the barrel 21 until the external threads of the needle 30 engage the internal threads of the barrel 20. The proximal tip 34 of the needle 30 has a luer lock connection or other fitting to permit a small pressure monitor 40 to be fastened directly to the device or connected via flexible tubing.

A stylet 41 is also provided for initial insertion into the barrel 20 when it is first introduced into the interspinous ligament of the patient.

In use, the barrel 20 and the stylet 41 are advanced as shown in FIG. 3 through the skin 42 and into the interspinous ligament. The stylet 41 is then removed from the barrel 20 as shown in FIG. 4 and the epidural needle 30 inserted between the spinous processes 44 and 45 of vertebrae 46 and 47. The pressure monitor or transducer 40 is attached and the tip 31 of the epidural needle 30 is advanced in a controlled manner by rotating the knurled wheel 33. The physician also presses the tab 22 against the skin of the patient to prevent the epidural needle 30 from pulling out of the patient. When a rapid decrease in pressure is observed, the tip 31 of epidural needle 30 has entered the epidural space and no further rotation of knurled wheel 33 is required. The pressure monitor 40 is then removed and anesthetic or other therapeutic agent administered.

The epidural needle placement device 10 of the present invention may be constructed of stainless steel, aluminum or another suitable metal or a suitable plastic material such as a high density polypropylene, polyester, or the like and may be prepared by conventional injection molding or similar techniques. The needle 30 can be constructed of stainless steel. Any suitable sized pressure monitor or transducer 40 that is commercially available may be used. Means other then threads may also be used to control the rate of advance of needle tip 31.

The invention has been described in detail with particular reference to certain preferred embodiments thereof, but it should be understood that variations and modifications can be effected within the spirit and scope of the invention.

What is claimed is:

1. An epidural needle placement device that comprises:
    a hollow barrel having a sharp tip at its distal end and internal threads on its proximal portion;
    a hollow epidural needle having a blunt tip at its distal end and external threads on its proximal portion that are adapted to engage the internal threads on said barrel;
    a flat tab that engages the barrel and is adapted to prevent penetration of the barrel into the epidural space of a patient;
    a knob that is affixed to the proximal end of the epidural needle that is adapted to advance the needle with respect to the barrel upon rotation of said knob; and
    a pressure monitor that is affixed to the proximal tip of the needle to monitor changes in pressure upon entry of the needle into the epidural space of the patient.

2. A method of inserting a hollow epidural needle into the epidural space of a patient that comprises the steps of:
    inserting an internally threaded hollow barrel of an epidural needle placement device through the skin of a patient;
    inserting an externally threaded hollow epidural needle into the barrel;
    engaging the threads of said needle with the threads of said hollow barrel;
    rotating the needle with respect to the barrel to advance the needle into the epidural space of the patient;
    monitoring the pressure; and
    stopping said rotation upon a sudden decrease in pressure which signifies entry of the needle into the epidural space of the patient.

* * * * *